(12) United States Patent
Belitsch et al.

(10) Patent No.: US 10,036,695 B2
(45) Date of Patent: Jul. 31, 2018

(54) VISCOSIMETER

(71) Applicant: ANTON PAAR GMBH, Graz-Strassgang (AT)

(72) Inventors: Wolfgang Belitsch, Hart Bei Graz (AT); Bernhard Leopold, Graz (AT)

(73) Assignee: Anton Paar GmbH, Graz-Strassgang (AT)

( * ) Notice: Subject to any disclaimer, the term of this patent is extended or adjusted under 35 U.S.C. 154(b) by 417 days.

(21) Appl. No.: 14/852,799

(22) Filed: Sep. 14, 2015

(65) Prior Publication Data

US 2016/0076986 A1    Mar. 17, 2016

(30) Foreign Application Priority Data

Sep. 12, 2014 (AT) ............................... A 50635/2014

(51) Int. Cl.
*G01N 11/14* (2006.01)

(52) U.S. Cl.
CPC ........ *G01N 11/14* (2013.01); *G01N 2011/145* (2013.01); *G01N 2011/147* (2013.01)

(58) Field of Classification Search
CPC ............. G01N 11/14; G01N 2011/145; G01N 2011/147
USPC .............................................. 73/54.28, 54.31
See application file for complete search history.

(56) References Cited

U.S. PATENT DOCUMENTS 7,441,442 B2 * 10/2008 Morgan .............. F16C 32/0446
73/54.28

FOREIGN PATENT DOCUMENTS

| AT | 40425 B | | 1/1910 |
| AT | 503994 A1 | | 2/2008 |
| AT | 507220 B1 | | 3/2010 |
| EP | 926481 | * | 6/1999 |
| JP | 2008020465 A | | 1/2008 |

* cited by examiner

*Primary Examiner* — Daniel S Larkin
(74) *Attorney, Agent, or Firm* — Laurence A. Greenberg; Werner H. Stemer; Ralph E. Locher

(57) ABSTRACT

A viscometer has a hollow cylinder mounted in a base frame and rotated about its longitudinal axis. A measuring part being flowed through by a fluid to be tested is rotatably supported in the hollow cylinder. An electromagnetic drive with a stator and a rotor for the hollow cylinder is provided, with which the hollow cylinder is rotatable. The stator is supported on the base frame and the rotor is supported on the hollow cylinder. An electromagnetic coupling of the stator with the rotor is provided by a ring rotor disposed between the stator and the rotor. The ring rotor is mounted about the longitudinal axis of the hollow cylinder so that the base frame and the hollow cylinder are decoupled with respect to the electromagnetic drive and a torque by the electromagnetic drive is applied to the hollow cylinder while the acting forces on the hollow cylinder are minimized.

20 Claims, 2 Drawing Sheets

VISCOSIMETER

CROSS-REFERENCE TO RELATED APPLICATION

This application claims the priority, under 35 U.S.C. § 119, of Austrian application AT A50635/2014, filed Sep. 12, 2014; the prior application is herewith incorporated by reference in its entirety.

BACKGROUND OF THE INVENTION

Field of the Invention

The invention relates to a viscosimeter.

There are measuring systems for the measurement of fluid properties, especially for viscosity, whose central part is a hollow cylinder filled with a liquid to be measured and rotating about its longitudinal axis, and in which a measuring part is rotatably mounted. The test fluid medium co-rotates along with the rotation of the outer measuring part or the hollow cylinder. This structure substantially corresponds to a viscometer according to the Couette principle, wherein the viscosity of the fluid between the concentric measuring parts, preferably cylinders, is determined from the self-adjusting balance between the outer hollow cylinder rotating at a constant speed and the co-rotating internal measuring part.

Reference is always made to a hollow cylinder in what follows, although the shape of the inner surface of this outer measuring part need not necessarily be cylindrical. The same applies to the outer surface of the inner measuring part. For example, the two measuring parts could each have the shape of two circular areas possessing adjoining truncated cones. The internal space of the outer measuring part and the outer surface of the inner measuring part should be at least axially symmetrical or be a body rotating with respect to the longitudinal axis of the hollow cylinder.

Viscometers are known according to the Couette principle using a variety of measurement and evaluation devices. For example, the self-adjusting angle or caster angle between the rotating outer and co-rotating inner measuring part can be measured—wherein both measuring parts rotate at the same speed—and the viscosity of the fluid can be determined from this. Another method is to measure the torque acting on the inner measuring part, wherein the inner measuring part remains, or is held, at rest. In general, the resulting data is detected by a sensor and transmitted to a control and evaluation unit.

Another variation of the measurement is possible by applying a braking torque to the inner measuring part or cylinder, and the viscosity of the medium between the cylinders can be determined from the self-adjusting speed difference between the two cylinders or measuring parts. Such arrangements use, in particular, a horizontal axis (see Austrian Patents/Applications AT 40425 B8, AT 503 994 A1). Other viscometers are known from Austrian Patent AT 507220 B1.

For various reasons—sample amount, cleaning, thermostatic control, etc.—, in order for a hollow cylinder to be able to be made as small as possible and be able to measure in the closed cell or in the flow, it is advantageous if the hollow cylinder can be so filled along its longitudinal or rotational axis that the sample fluid enters the hollow cylinder on one side and exits it on the opposite side. In order to ensure that the sample to be measured is free of air bubbles on refilling without intermediate purging, it is advantageous if the hollow cylinder is not closed or flowed through during rotation. This represents a challenge for the seal, the bearing and the drive of the hollow cylinder.

The prior art provides various options for the sealing and bearing of a rotating hollow cylinder. They all have the disadvantage that complete sealing cannot be ensured in the long term. It is therefore an object of the invention to keep the number of sealing rotating elements as low as possible.

The rotation of the hollow cylinder is generally carried out with the aid of an electric motor, wherein there are various possibilities for transferring the rotation of the electric motor to the hollow cylinder.

Another possibility is a concentric drive. In this case, the hollow cylinder and the motor have a common axis of rotation. The drive of the hollow cylinder can be made via a shaft. This has the disadvantage that a further sealing element is necessary for the shaft, which leads to another potential leak site, and creates a further point with wearing parts.

Another possibility for a drive is a magnetic coupling. However, experience shows that the non-constant friction on the bearings of the hollow cylinder leads to rotary oscillating movements, and a sufficiently uniform rotation of the hollow cylinder is not possible. In addition, the radial and axial forces are detrimental to the bearing and accurate measurement.

Eccentric drives can be implemented in various ways, such as via gears, belts, etc. In addition to the disadvantage of lateral forces, which are very disadvantageous for the bearing in the case of small versions of the system, any leakage at the rotary seal of the hollow cylinder might possibly allow problematic sample liquid to penetrate into areas where it may present a threat or cause damage. Such arrangements have the disadvantage that additional seals and/or bearings are required.

Japanese Patent Application JP 2008020465 A discloses a system in which a stepper motor directly drives the measuring cup.

SUMMARY OF THE INVENTION

The aim of the invention is primarily the creation of a viscometer with a drive for a hollow cylinder filled with a sample liquid, wherein the drive does not require complex sealing, and, in addition, allows encapsulation of the hollow cylinder, and, in the event of leakage of the seals, itself prevents leakage of sample fluid into areas that the sample liquid must not enter. At all events, thermostatic control of the sample liquid should be easily possible at least in the rotating area. In addition, thermostatic control of the non-rotating area should be possible.

According to the invention, it is thus provided that, for the electro-magnetic coupling of the stator to the rotor, a ring rotor driven by the stator is rotatably mounted between the stator and the rotor in order to rotate about the longitudinal axis of the hollow cylinder, so that the base frame and the hollow cylinder are mechanically decoupled with respect to the electro-magnetic drive, and the specified torque is transferable to the hollow cylinder via the electromagnetic drive, while the axial and radial forces acting on the hollow cylinder are minimized.

The drive of the viscometer according to the invention thus contains an electric motor, the stator of which is fixedly connected to the non-rotating part of the measuring system or the basic frame, while the rotor is fixedly connected to the rotating hollow cylinder. In this case, all types of stators of electric motors (direct current, synchronous, asynchronous, stepping motor), which are suitable for a continuous rotation of a rotor or, as in the present case, for the drive of the ring traveller, become possible.

According to the invention, disturbing forces that falsify measurements are prevented from acting on the hollow cylinder. In addition, the stator is thermally separated from the hollow cylinder and the temperature control of the measuring fluid is usually carried out via a tempering block surrounding the rotor.

The disadvantages of the known prior art arrangements, wherein at least one additional seal is necessary in order to make the drive fluid-tight, are avoided.

The use of conventional hollow shaft motors or stepper motors is not possible because of the thermal sensitivity of such measurements and the mechanical sensitivity of the measuring system to lateral forces that can be applied to the rotor in the system via the drive. However, mechanical and thermal decoupling is possible by means of the invention.

The invention thus solves the problem of creating a special drive for a hollow cylinder that is thermally and mechanically decoupled from the base frame in a viscometer with a preferably horizontal orientation of the rotation axis of the hollow cylinder, because a hollow shaft motor directly seated on the hollow cylinder produces heat in operation, which would thus interfere with the sensitive and highly accurate temperature control of the system.

The major disadvantage of all the known embodiments is remedied, namely the admittedly small but disturbing forces in the axial and radial directions that mitigate against further miniaturization. Eddy current coupling is provided between the ring rotor of the electromagnetic drive and the rotating hollow cylinder in order to minimize these forces acting on the bearing of the rotor. To this end, the ring rotor of the electromagnetic drive carries permanent magnets that drive the eddy current body or annular flange on the rotary hollow cylinder, while the ring rotor itself is rotatably supported by the stator on the fixed part or base frame of the viscometer. Another advantage of this eddy current coupling is that it has a damping effect and thus does not adversely affect the stability of the speed of the hollow cylinder to be rotated through disturbing fluctuations in the speed of the electric motor. An advantage of rotating magnets, when compared with a rotating field generated by coils, is that the coils must be large in size in order to achieve the necessary magnetic field strength, and, due to this size, the considerable power required produces heat. Thus, permanent magnets are preferable to coils.

In order to protect the stator and the permanent magnets and the bearings of the ring rotor from possible aggressive sample or cleaning fluids, a membrane or membrane disk or fluid-tight insulating layer is provided between the stator and the rotating system of permanent magnets including the bearing on the one hand, and the rotating hollow cylinder carrying the eddy current body on the other.

According to the invention, a three-part motor is created that consists of a coil arrangement of a stator driven by a ring rotor carrying bearing-supported rotating permanent magnets, which in turn produce an eddy current drive of the measuring cup or hollow cylinder.

When one considers known hollow motors with a stator plus coils and a rotor—for example with magnets—then one knows the slip-stick effects associated with the drive, which occur both axially and radially and lead to undesirable forces. Both effects can load the fluid bearing, for example axially, so that the bearings begin to leak. The radial load on the bearing of the hollow cylinder may even cause the shaft to jump out of the bearing. Such loads are avoided with the invention.

The drive according to the invention thus enables substantial miniaturization.

In accordance with an embodiment of the invention, the ring rotor is supported on the base frame or on an axis of rotation of the base frame. The permanent magnets, the electromagnets or the windings disposed on the ring rotor are disposed opposite the electromagnetic coil or the electromagnet of the stator when seen in an axial direction or radial direction of the hollow cylinder.

In accordance with a further embodiment of the invention, the annular flange extends radially away from an outer wall of the hollow cylinder and extends without interruption around the hollow cylinder.

Other features which are considered as characteristic for the invention are set forth in the appended claims.

Although the invention is illustrated and described herein as embodied in a viscosimeter, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 1:
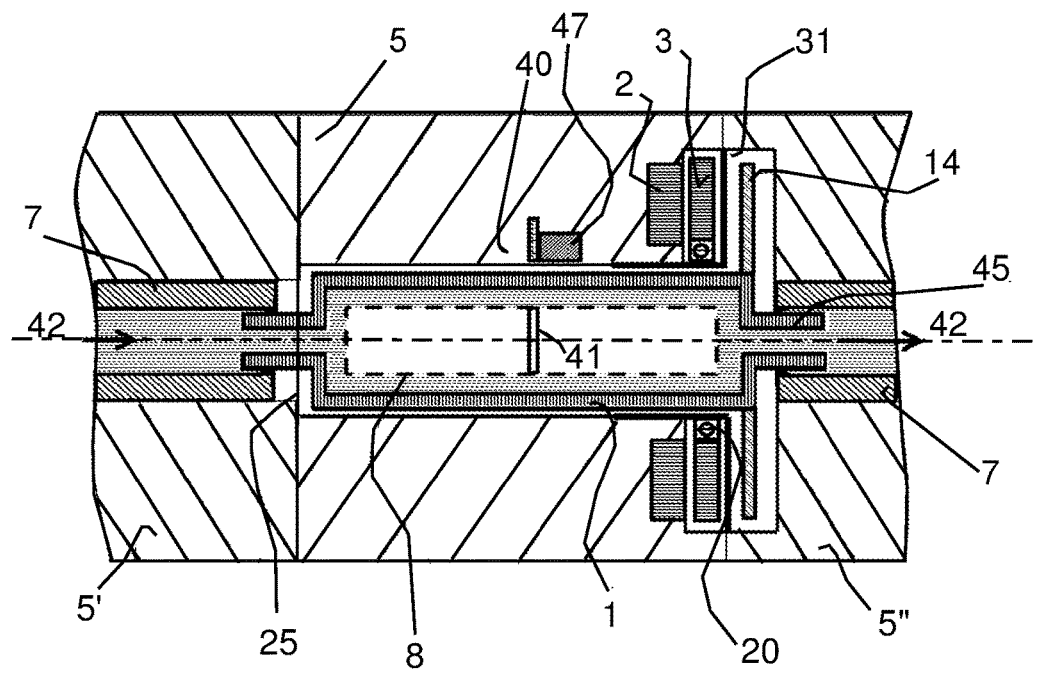
FIG. 1 is a diagrammatic, longitudinal sectional view through the section or part of a viscometer that is key for a measurement according to the invention.

Referring now to the figures of the drawings in detail and first, particularly to FIG. 1 thereof, there is shown a viscometer according to the invention which has a base frame 5, in which is formed an advantageously cylindrically-shaped receiving or hollow space 25 with which a hollow cylinder 1 is incorporated. As already mentioned, the hollow cylinder 1 need not necessarily have a cylindrical outer shape; the external surfaces or the generatrix may also be inclined, so that other geometrical bodies can be used, in particular that are rotationally symmetrical to the longitudinal axis of the hollow cylinder 1.

The hollow cylinder 1 is mounted in a fluid-tight bearing 7 in its two end areas. For this purpose, pipe sockets 45 are connected or integrally formed at the end areas or end surfaces of the hollow cylinder 1, and with which the hollow cylinder 1 is supported in the bearing 7. The pipe sockets 45 allow measuring fluid to pass through the hollow cylinder 1, for example in the direction of the arrow 42.

Advantageously, there is also a rotationally-symmetrical, in particular, cylindrically-shaped measuring part 8 inside the hollow cylinder 1. In principle, this measuring part 8 could have a cross-section in the shape of a polygon.

For a measurement, the hollow cylinder 1 is rotated in an internal space 25 of the base frame 5. The measuring part 8 located in the hollow cylinder 1 will co-rotate with the measuring fluid flowing through the hollow cylinder 1. The measuring part 8 floats in the fluid and rotates at a substantially lower speed than the hollow cylinder 1 due to a braking effect caused by the interaction of permanent magnets 41 in the measuring part 8 with an electrically-conductive eddy current body 40 or soft iron ring that is rigidly connected to the base frame 5. A speed difference between the hollow cylinder 1 and the measuring unit 8 can be used as a measure for the viscosity of the liquid and analysed. The measuring part 8 in the internal space of the hollow cylinder 1 can be stabilized with respect to its location in the longitudinal and/or lateral directions, for example through interacting magnets or a combination of a soft iron ring 40 on the base frame 5 and the magnet 41 on the measuring part 8. These arrangements essentially fix the hollow cylinder 8 with respect to its axial position or in the longitudinal direction of the hollow cylinder 1. The rotational speed of the measuring part 8 can be determined, for example, by a Hall sensor 47 and the magnet 41.

At least a coil or at least a winding or at least an electromagnet is arranged in the base frame 5 as the stator 2 of an electromagnetic drive of the hollow cylinder 8 used for the rotary drive of the hollow cylinder 1. The drive of the hollow cylinder 1 is, however, not direct, but is via a ring rotor 3 with a bearing 20 mounted on the base frame 5, and which lies in front of the stator 2. The ring rotor 3 is mounted on the base frame 5 or on the axis of rotation of the base frame 5 and carries permanent magnets, electromagnets or coils which interact with the respective permanent magnets, electromagnets or windings on the base frame 5, i.e. the stator 2. The ring rotor 3 rotates around the longitudinal axis 24 of the hollow cylinder 1 driven by the stator 2 and induces eddy currents in a rotor 14 carried by the hollow cylinder 1 and which cause a rotation of the rotor 14 and the hollow cylinder 1.

The base frame 5 or the stator 2 on the one hand, and the hollow cylinder 1 on the other, are thus mechanically decoupled with respect to the electromagnetic drive. Nevertheless, a predetermined torque can be transmitted to the hollow cylinder 1, wherein, however, undesirable axial and radial forces simultaneously acting on the hollow cylinder 1 are minimized. The annular flange 4 forming the rotor 14 is made of electrically-conductive, but non-magnetic and non-magnetisable material, while the ring rotor 3 driven by the eddy currents induced in the annular flange 4 by the ring rotor 3.

To minimize the forces acting on the hollow cylinder 1, the stator 2, the ring rotor 3 and the rotor 14 formed as a ring flange 4 are successively mounted side by side within the base frame 5 in the axial direction of the hollow cylinder 1.

Figure 2:
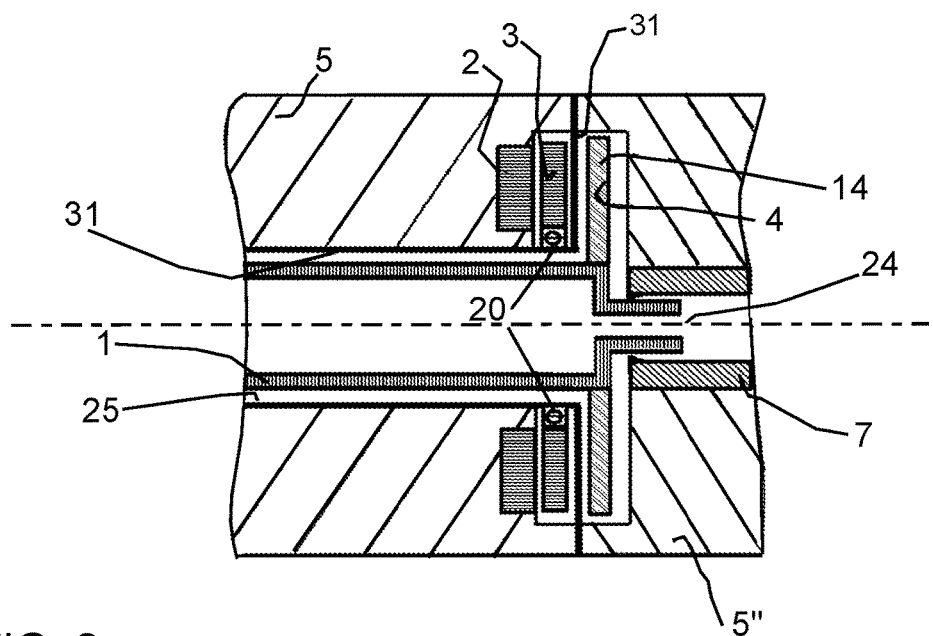
FIG. 2 is a detailed sectional view of a part of FIG. 1.

Furthermore, it is useful if—as shown in FIGS. 1 and 2—the stator 2 and the ring rotor 3 and the bearing 20 carrying the ring rotor 3 are encapsulated fluid-tight against the internal space 25 of the base frame 5 receiving the hollow cylinder 1, in particular by a fluid-tight membrane 31. In this way, in the event of an exit of test fluid from the hollow cylinder 1, or if leakage occurs at the bearing 7 for the pipe socket 45 of the hollow cylinder 1, it is possible to avoid contact of the test fluid with the stator 2 and the ring rotor 3.

As shown in FIGS. 1 and 2, the left and right sections 5', 5" of the base frame 5 can be separated from the base frame 5, or the bearing 7 located there can be removed from the connecting piece or pipe socket 45 of the hollow cylinder 1, so that access to the hollow cylinder 1 or replacement of the bearing 7 is also possible.

Figure 3:
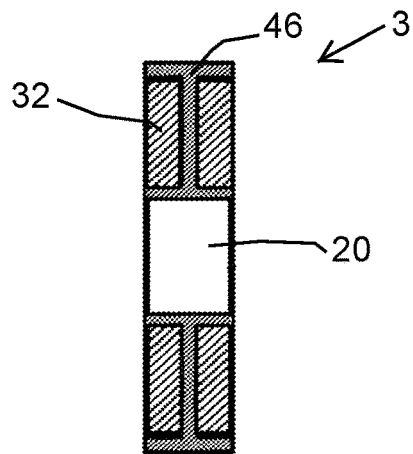
FIG. 3 is a section view of a ring motor.
Figure 4:
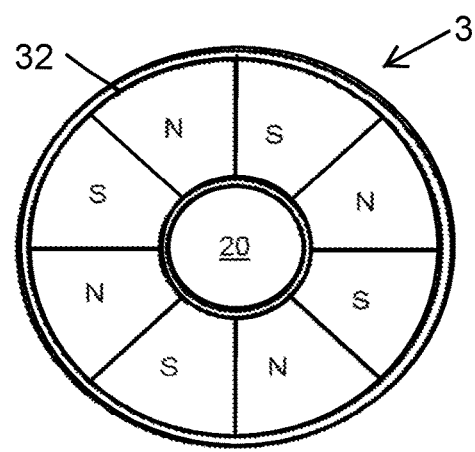
FIG. 4 is a front view of the ring rotor.

FIGS. 3 and 4 show a front view and a sectional view of an embodiment of the ring rotor 3. An annular support 46 is mounted on a bearing 20, carrying permanent magnets 32 arranged on both sides around the periphery of the annular support 46 with alternating polarity. Such a ring rotor 3 is rotated by the stator 2 located on the base frame 5 and which, itself, in turn, rotates the rotor 14 carried by the hollow cylinder 1.

Figure 5:
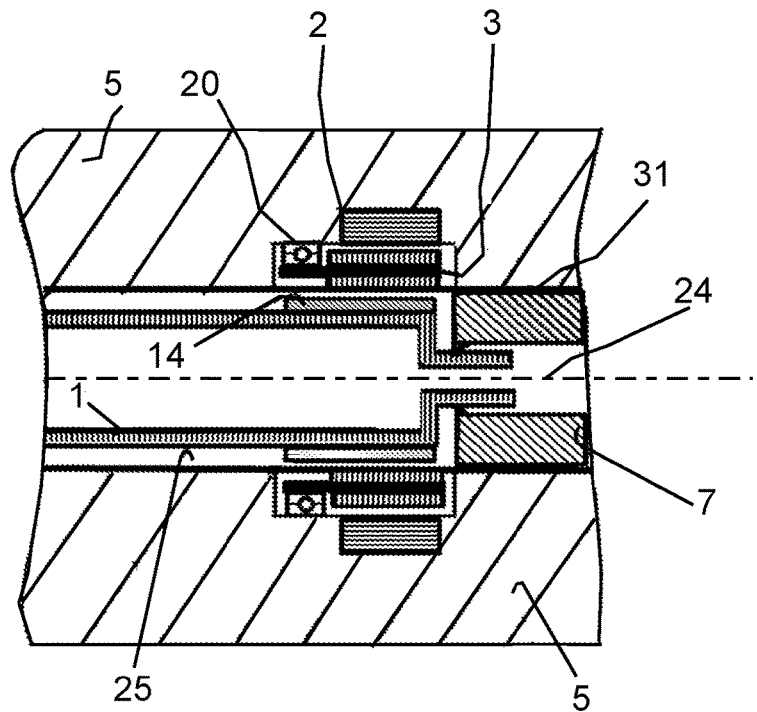
FIG. 5 is a sectional view of an alternative embodiment of the viscometer, the control and drive units for the electromagnetic drive as well as the detectors and evaluation units for the measured data are not shown as these units and their connection are known to a person of average skill in the art.

FIG. 5 shows an alternative embodiment wherein the ring rotor 3 supported by the bearing 20 lies radially inwards, or in front, of the stator 2. A rotor 14 has a hollow cylinder or ring member, which is supported by the hollow cylinder 1, surrounds the latter and is arranged radially inwards of the ring rotor 3.

The invention claimed is:

1. A viscometer, comprising:
   a base frame;
   a hollow cylinder mounted in said base frame and rotating about a longitudinal axis;
   a rotatably-mounted measuring part through which a fluid being tested flows and disposed within said hollow cylinder;
   an electromagnetic drive having a stator and a rotor with which said hollow cylinder being rotatable in said base frame, said stator supported on said base frame and said rotor supported on said hollow cylinder; and
   a ring rotor rotatably supported between said stator and said rotor, said ring rotor providing an electromagnetic coupling of said stator with said rotor, said ring rotor being driven by said stator about the longitudinal axis of said hollow cylinder, so that said base frame and said hollow cylinder are mechanically decoupled with respect to said electromagnetic drive, and a predetermined torque is transferable to said hollow cylinder via said electromagnetic drive, while forces acting axially and radially on said hollow cylinder are simultaneously minimized.

2. The viscometer according to claim 1, further comprising fluid-tight sealing bearings, said hollow cylinder is rotatably mounted at opposite end areas with said fluid-tight sealing bearings in said base frame.

3. The viscometer according to claim 1, wherein said hollow cylinder has a through-flow opening formed therein or a connecting pipe socket at each of its two ends.

4. The viscometer according to claim 1, wherein:
   said stator is selected from the group consisting of an electromagnetic coil, electromagnetic winding, and an electromagnet and is disposed on said base frame;
   said ring rotor has a supporting ring; and
   said ring rotor has permanent magnets, electromagnets or a plurality of windings, said permanent magnets, said electromagnets or said windings disposed side-by-side on said supporting ring of said ring rotor with alternating polarity.

5. The viscometer according to claim 4, wherein:
   said ring rotor is supported on said base frame or on an axis of rotation of said base frame; and
   said permanent magnets, said electromagnets or said windings disposed on said ring rotor are disposed opposite said electromagnetic coil or said electromagnet of said stator when seen in an axial direction or radial direction of said hollow cylinder.

6. The viscometer according to claim 4, wherein said hollow cylinder, in an area of its rotational axis or the longitudinal axis, has a through-flow opening formed therein or a connecting pipe socket at each of its two ends.

7. The viscometer according to claim 4, wherein said stator surrounds said hollow cylinder.

8. The viscometer according to claim 4,
further comprising a carrier; and
wherein said rotor is an annular flange disposed at an end area of said hollow cylinder, directly extending away from or supported by said hollow cylinder in an end area of said hollow cylinder, by said carrier extending from said hollow cylinder and supporting said annular flange.

9. The viscometer according to claim 1,
further comprising a carrier; and
wherein said rotor is an annular flange directly extending away from or supported by said hollow cylinder and in an end area of said hollow cylinder, by said carrier extending from said hollow cylinder and supporting said annular flange.

10. The viscometer according to claim 9, wherein said annular flange extends radially away from an outer wall of said hollow cylinder and extends around said hollow cylinder.

11. The viscometer according to claim 1, further comprising a bearing supported on said base frame, said ring rotor is rotatable around said hollow cylinder on said bearing.

12. The viscometer according to claim 11, wherein:
said base frame has a receiving internal space formed therein; and
said stator, said ring rotor, and said bearing carrying said hollow cylinder are covered or encapsulated fluid-tight against said receiving internal space of said base frame.

13. The viscometer according to claim 12, further comprising a fluid-tight membrane for forming a fluid tight connection between said stator, said ring rotor, and said bearing carrying said hollow cylinder and said receiving internal space of said base frame.

14. The viscometer according to claim 11, wherein said bearing surrounds said hollow cylinder.

15. The viscometer according to claim 1, wherein said rotor is formed from a further hollow cylinder or a ring member connected with said hollow cylinder and surrounding said hollow cylinder, said ring rotor is disposed or rotates radially inside said stator and radially outside said rotor.

16. The viscometer according to claim 15, wherein said annular flange or said ring member forming said rotor is made of an electrically-conductive material and can be driven by said ring rotor due to eddy currents induced in said annular flange by said ring rotor.

17. The viscometer according to claim 16, wherein said electrically-conductive material is non-magnetic and non-magnetisable, and is a metal.

18. The viscometer according to claim 15, wherein said hollow cylinder carried by said rotor is exclusively driven by eddy currents induced in said annular flange or said ring member of said rotor by said ring rotor.

19. The viscometer according to claim 1, wherein said stator, said ring rotor and said rotor in a form of an annular flange on said base frame are disposed successively side-by-side in an axial direction or a radial direction of said hollow cylinder.

20. The viscometer according to claim 1, wherein the longitudinal axis of said hollow cylinder and an axis of rotation of said ring rotor coincide with one another.

\* \* \* \* \*